(12) United States Patent
Baillargeon et al.

(10) Patent No.: US 11,857,365 B2
(45) Date of Patent: Jan. 2, 2024

(54) DUAL LUMEN CATHETER

(71) Applicant: OLYMPUS MEDICAL SYSTEMS CORPORATION, Hachioji (JP)

(72) Inventors: Jean-Martin Baillargeon, Seattle, WA (US); Jason T. Panzenbeck, Seattle, WA (US)

(73) Assignee: Olympus Medical Systems Corporation, Tokyo (JP)

( * ) Notice: Subject to any disclaimer, the term of this patent is extended or adjusted under 35 U.S.C. 154(b) by 1130 days.

(21) Appl. No.: 16/360,797

(22) Filed: Mar. 21, 2019

(65) Prior Publication Data
US 2020/0297311 A1   Sep. 24, 2020

(51) Int. Cl.
| | |
|---|---|
| *A61B 8/00* | (2006.01) |
| *A61B 1/00* | (2006.01) |
| *A61B 1/012* | (2006.01) |
| *A61B 1/018* | (2006.01) |
| *A61B 8/12* | (2006.01) |
| *A61B 1/267* | (2006.01) |
| *A61M 25/00* | (2006.01) |
| *A61M 25/01* | (2006.01) |

(52) U.S. Cl.
CPC .......... *A61B 8/445* (2013.01); *A61B 1/00066* (2013.01); *A61B 1/00135* (2013.01); *A61B 1/00137* (2013.01); *A61B 1/018* (2013.01); *A61B 1/0125* (2013.01); *A61B 1/2676* (2013.01); *A61B 8/12* (2013.01); *A61B 8/4494* (2013.01); *A61M 25/0026* (2013.01); *A61M 25/0136* (2013.01); *A61M 2025/0037* (2013.01)

(58) Field of Classification Search
CPC . A61B 8/445; A61B 1/00066; A61B 1/00135; A61B 1/00137; A61B 1/0125; A61B 1/018; A61B 1/2676; A61B 8/12; A61B 8/4494; A61B 1/00073; A61M 25/0026; A61M 25/0136; A61M 2025/0037; A61M 25/0032

See application file for complete search history.

(56) References Cited

U.S. PATENT DOCUMENTS

| | | | |
|---|---|---|---|
| 4,798,193 A | 1/1989 | Giesy et al. | |
| 5,421,338 A * | 6/1995 | Crowley | A61B 8/4461 600/463 |
| 5,899,882 A * | 5/1999 | Waksman | A61N 5/1002 604/523 |
| 6,299,599 B1 * | 10/2001 | Pham | A61F 7/123 604/113 |
| 6,394,141 B2 * | 5/2002 | Wages | B29C 48/302 138/116 |
| 6,544,230 B1 * | 4/2003 | Flaherty | A61B 17/3207 604/164.12 |

(Continued)

*Primary Examiner* — Sanjay Cattungal
(74) *Attorney, Agent, or Firm* — Schwegman Lundberg & Woessner, P.A.

(57) ABSTRACT

A catheter and catheter system includes a first lumen and a second lumen adjacent to the first lumen. The catheter occupies an arc around the first lumen, wherein the arc is greater than 180° and less than 360°, thus creating a lengthwise opening to the first lumen. The catheter material surrounds the second lumen in a cross-sectional dimension. Prior to a procedure, a sampling device is introduced into the second lumen prior and the probe is snapped into the first lumen prior to insertion into an endoscope.

20 Claims, 4 Drawing Sheets

(56) References Cited

U.S. PATENT DOCUMENTS

| | | | |
|---|---|---|---|
| 7,322,953 B2* | 1/2008 | Redinger | A61M 25/0043 604/43 |
| 7,654,978 B2* | 2/2010 | Wahr | A61B 17/12109 604/96.01 |
| 8,562,557 B2* | 10/2013 | Chesnin | A61M 25/0021 604/43 |
| 10,292,807 B2 | 5/2019 | Wilson et al. | |
| 11,324,526 B2* | 5/2022 | Yurek | A61M 1/85 |
| 2002/0156521 A1* | 10/2002 | Ryan | A61F 2/90 623/1.13 |
| 2006/0265043 A1* | 11/2006 | Mandrusov | A61M 1/3613 623/1.42 |
| 2008/0154345 A1* | 6/2008 | Taylor | A61B 1/3137 607/93 |
| 2009/0005757 A1* | 1/2009 | Taber | A61M 25/0074 600/585 |
| 2009/0312687 A1* | 12/2009 | DeFonzo | A61M 1/30 604/6.16 |
| 2013/0053763 A1* | 2/2013 | Makino | A61M 25/003 604/523 |
| 2014/0135576 A1* | 5/2014 | Hebert | A61B 1/012 600/109 |
| 2015/0359998 A1* | 12/2015 | Carmel | A61M 25/0075 604/509 |
| 2016/0220302 A1* | 8/2016 | Zarins | A61B 8/0841 |
| 2016/0279388 A1* | 9/2016 | Barrish | A61M 25/1034 |
| 2017/0128639 A1* | 5/2017 | Erbey, II | A61M 25/1025 |
| 2017/0224956 A1* | 8/2017 | Melsheimer | A61B 1/0055 |
| 2018/0028787 A1* | 2/2018 | McNiven | A61B 5/6852 |
| 2020/0146757 A1* | 5/2020 | Fenech | A61B 34/10 |
| 2020/0171274 A1* | 6/2020 | Jonkman | A61M 1/3659 |
| 2021/0023359 A1* | 1/2021 | Kojo | A61B 1/233 |
| 2021/0121188 A1* | 4/2021 | Yurek | A61M 1/85 |

\* cited by examiner

DUAL LUMEN CATHETER

BACKGROUND

The tools that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (rEBUS) probe is then threaded through the guide sheath and used to determine the approximate location of the tumor.

Currently, there is limited room in the working channel of an endoscope (e.g., bronchoscope) for an ultrasound probe and medical device (e.g., a needle) delivered in a conventional dual-lumen catheter without having to shrink the size of current off-the-shelf ultrasound probes and/or medical devices.

SUMMARY

The present disclosure describes an improved guide sheath for use with a medical scope, such as a bronchoscope.

An exemplary catheter includes a first lumen and a second lumen adjacent to the first lumen. The catheter occupies an arc around the first lumen, wherein the arc is greater than 180° and less than 360°, thus creating a lengthwise opening to the first lumen. The catheter material surrounds the second lumen in a cross-sectional dimension.

In one aspect, the second lumen has a smaller inner diameter than the first lumen. Also, the catheter can be slidably received within a working channel of an endoscope.

In another aspect, the second lumen can slidably receive a medical device and the first lumen can receive an imaging device. The imaging device includes a probe.

In still another aspect, the lengthwise opening of the first lumen is defined by a first flexible edge and a second flexible edge. A first chord measurement between the first and second edges has a first value when the imaging device is not occupying the first lumen. A second chord measurement between the first and second edges has a second value when the imaging device is occupying the first lumen. The first chord measurement is less than the second chord measurement.

In yet another aspect, the first and second edges exhibit a snap-like action upon receiving the imaging device.

In still yet another aspect, a needle is introduced into the second lumen prior to the procedure and the probe is snapped into the trough (first lumen) prior to insertion into an endoscope.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses. The invention improves the ability HCPs to sample tissue or deliver substances with real-time feedback.

Figure 1:
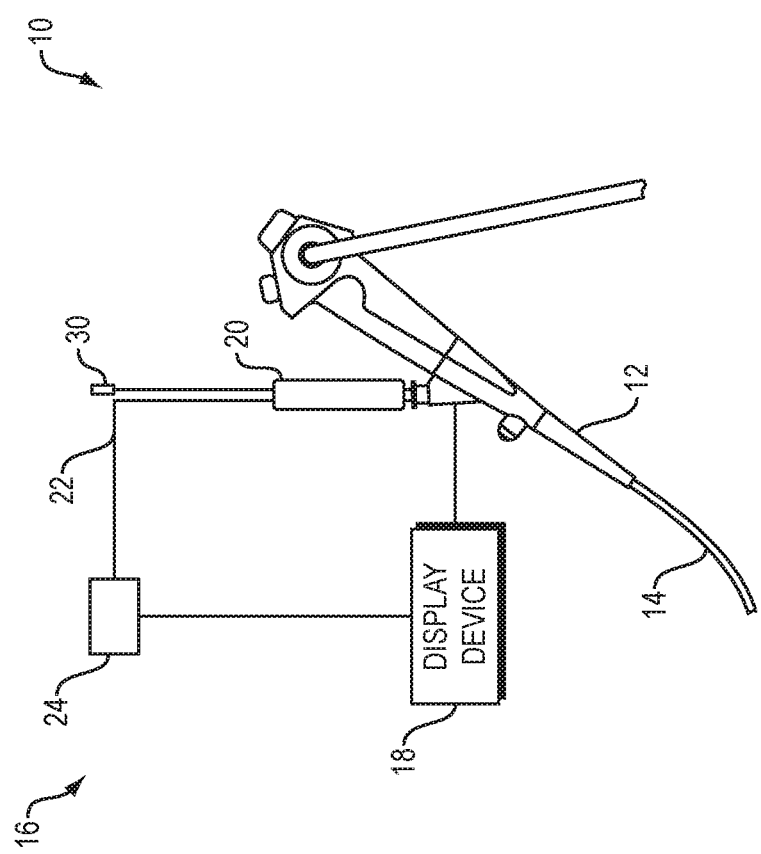
FIG. 1 illustrates an example of a bronchoscope system formed in accordance with an embodiment of the disclosure.

Referring now to FIG. 1, a bronchoscope system 10 includes a bronchoscope 12 with an insertion tube 14, a radial ultrasound system 16 and an access device 20. The radial ultrasound system 16 includes a signal processor 24, a display device 18 and a radial ultrasound probe 22. The radial ultrasound probe 22 and a medical device 30, such as a needle for sampling and/or medicant delivery, are received within the bronchoscope 12 via a handle component and a sheath/catheter component of the access device 20.

The display device 18 is in wired or wireless signal communication with the bronchoscope 12 and/or the signal processor 24. The display device 18 presents images generated based on information received from the bronchoscope 12 and/or the signal processor 24 that receives image information from a radial ultrasound transducer at the distal end of the radial ultrasound probe 22. A diagnostic endoscope (e.g., BF series produced by Olympus®) is an example of the bronchoscope 12 and the radial endobronchial ultrasound (rEBUS) probes produced by Olympus® are examples of the radial ultrasound device 16.

Figure 2:
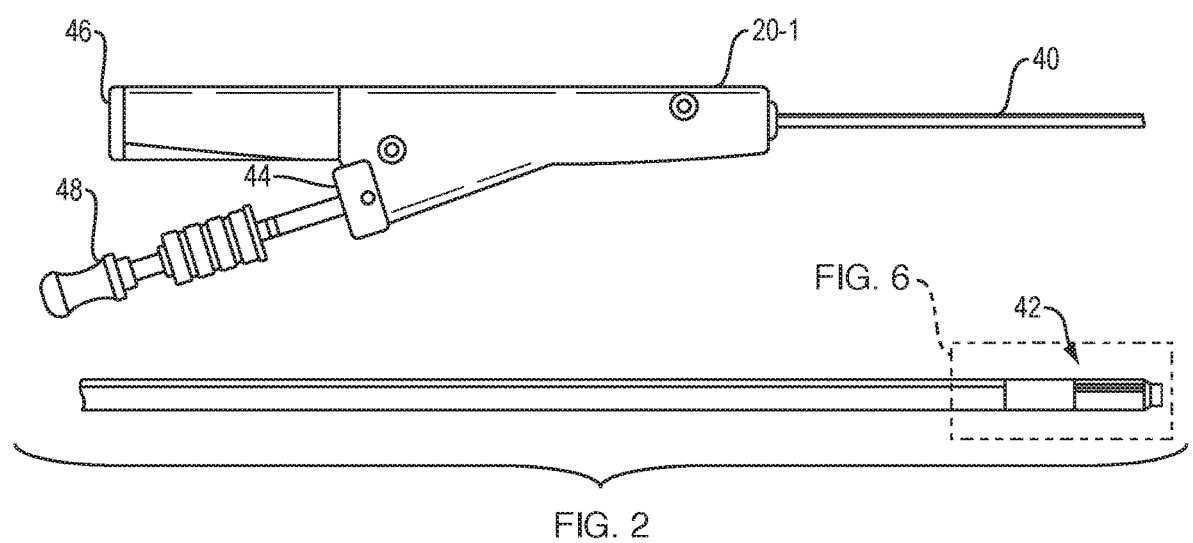
FIG. 2 is a side view of a real-time system formed in accordance with an embodiment of the disclosure.

FIG. 2 illustrates an access device 20-1 that includes a two-port handle component 32 that attaches to a dual-lumen catheter 40. Attached at a distal end of the dual-lumen catheter 40 is a cap 42. As will be shown in more detail below, the dual-lumen catheter 40 includes a fully enclosed lumen that is in communication with a first access port 44 of the two-port handle component 32 and an open trough that is in communication with a second access port 46 of the two-port handle component 32. The first access port 44 is configured to receive a medical device 48, such as a needle, and direct the medical device into the enclosed lumen within the dual-lumen catheter 40. The second access port 46 is configured to receive and direct the radial ultrasound probe 22 into the open trough of the dual-lumen catheter 40.

In one embodiment, the two-port handle component 32 may include a hinged door or removable section that allows access to an internal lumen that connects the second access port 46 to the open trough of the dual-lumen catheter 40. When the hinged door or removable section is in an opened configuration, the internal lumen is made accessible such that the radial ultrasound probe 22 may be placed directly into the internal lumen. This allows one to simultaneously place a shaft of the radial ultrasound probe 22 into the internal lumen of the two-port handle 32 and into the open trough of the dual-lumen catheter 40.

Figure 3:
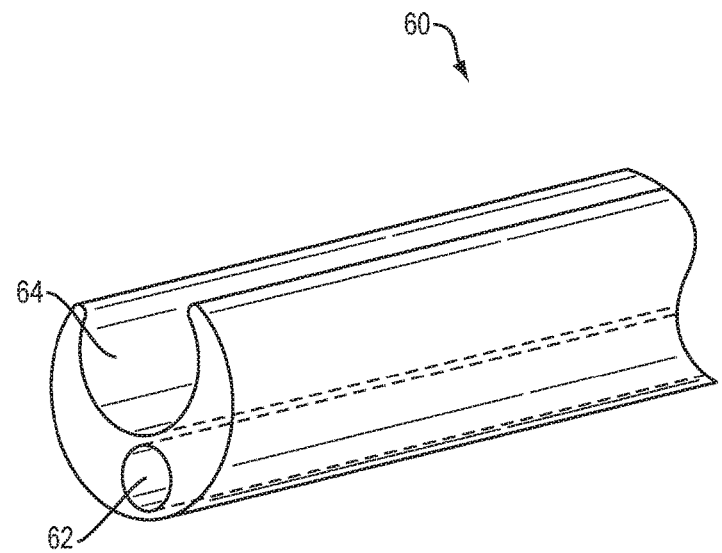
FIG. 3 is a perspective, x-ray view of a distal portion of a catheter included in the device shown in FIG. 2.
Figure 4:
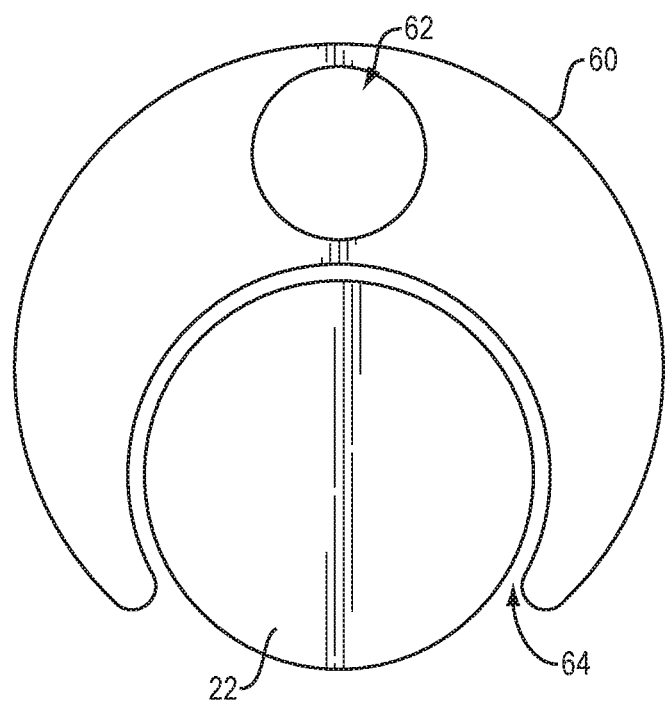
FIG. 4 is a plan view of the distal end of the catheter shown in FIG. 3.

FIGS. 3 and 4 illustrates views of an exemplary dual-lumen catheter 60. The dual-lumen catheter 60 includes a first enclosed lumen 62 configured to receive a medical device. The dual-lumen catheter 60 includes a second lumen 64 sized to receive the radial ultrasound probe 22. The second lumen 64 is not fully enclosed by the material of the dual-lumen catheter 60. The second lumen 64 has a cross-section similar to that of a trench, trough or open channel. The second lumen 64 includes a central axis that is offset from a central axis of the dual-lumen catheter 60. The position of the central axis of the second lumen 64 relative to the central axis of the dual-lumen catheter 60 is selected that when the radial ultrasound probe 22 is inserted into the second lumen 64, the outer surface of the radial ultrasound probe 22 that is exposed is at a distance from the central axis of the dual-lumen catheter 60 that is between being slightly less to slightly greater than the actual radius of the dual-lumen catheter 60. Thus, because the dual-lumen catheter 60 does not occupy the space fully around the second lumen 64, the overall diameter of the dual-lumen catheter 60 can be optimized. In other words, the size of the first and second lumens 62, 64 can be maximized.

In one embodiment, the position of the central axis of the second lumen 64 relative to the central axis of the dual-lumen catheter 60 and dimensions of the second lumen 64 are selected so that the radius of the second lumen 64 extends at least as radially as the radius of the dual-lumen catheter 60.

In one embodiment, the edges of the dual-lumen catheter 60 that define the opening of the second lumen 64 are made of a material that allows them to expand to a more open configuration to allow the radial ultrasound probe 22 to be inserted collaterally versus being slid into the second lumen 64 from the proximal end. The material may include a variety of thermoplastics (Pebax, polyurethane, PEEK, etc.) or thermoset (silicone, PTFE). The material around the second lumen 64 trough should be rigid enough to hold the probe 22, yet flexible enough to allow a snapping-in of the probe 22. The insertion of the radial ultrasound probe 22 into the second lumen 64 may cause a clicking action or noise caused be the edges of the dual-lumen catheter 60 snapping back after being expanded to allow for the diameter of the probe 22.

Figure 5:
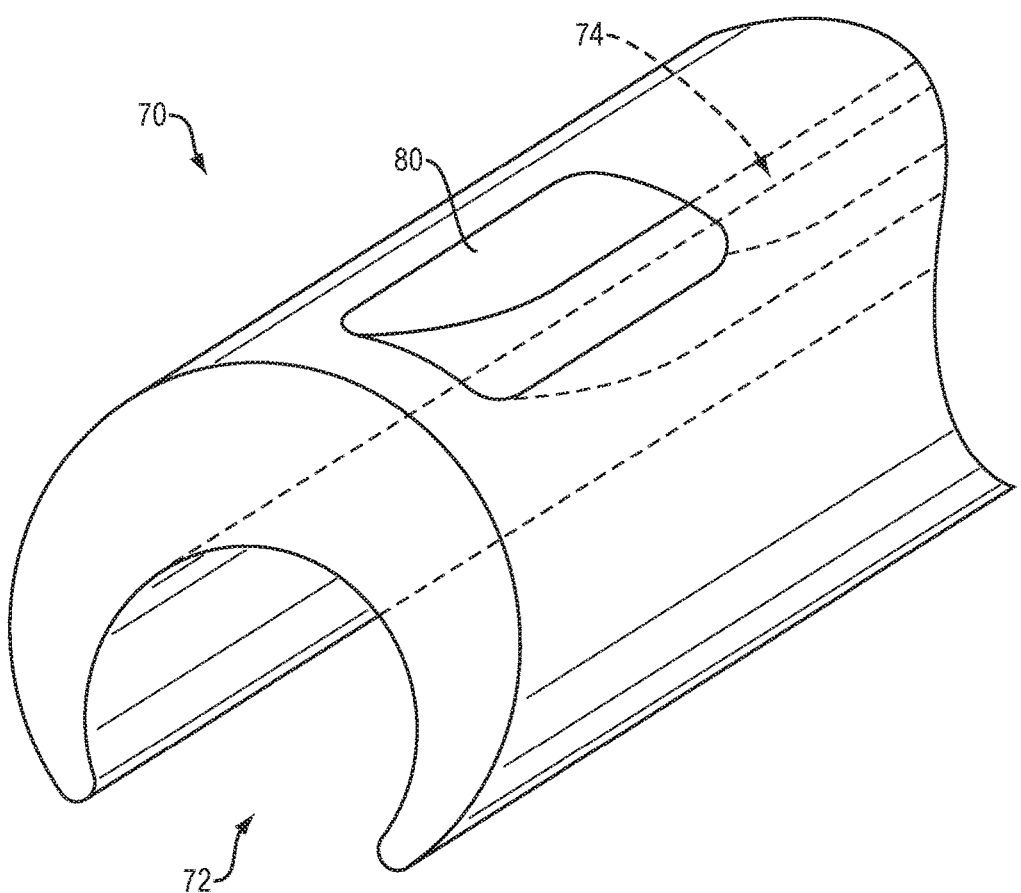
FIG. 5 is a perspective, x-ray view of a catheter formed in accordance with an embodiment of the disclosure.
Figure 6:
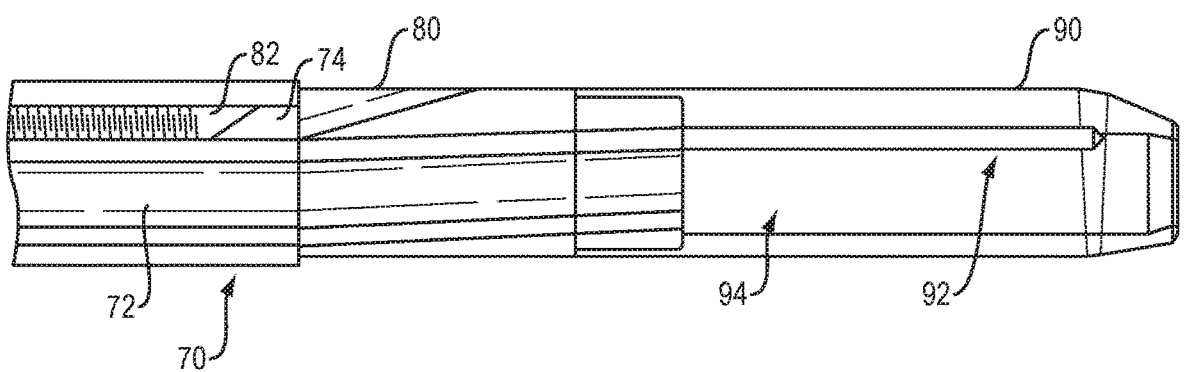
FIG. 6 is a side, x-ray view of the distal end of a catheter system formed in accordance with an embodiment of the disclosure.

As shown in FIGS. 5 and 6, a dual-lumen catheter 70 includes an open lumen 72 and a medical device lumen 74. At a distal end of the dual-lumen catheter 70 an exit port 78 provides access to the medical device lumen 74. A ramp 80 at the exit port 78 allows a medical device 82 to be directed out of the exit port 78.

In one embodiment, a cap section 90 is attachable to the distal end of the dual-lumen catheter 70. The cap section 90 includes a lumen 94 for receiving a radial ultrasound probe and one or more lumens for receiving one or more orientation pins 92. In one embodiment, a ramp 80-1 may also be included in the cap section 90 instead of being included in the catheter.

The orientation pins provide an echogenic feature, thus providing more visibility in the ultrasound image and thus alert the user to the rotational orientation of the distal end of the access device 20 and the needle relative to a target.

Embodiments

A. A catheter comprising: a first lumen; and a second lumen adjacent to the first lumen; wherein material of the catheter occupies an arc around the first lumen, wherein the arc is greater than 180° and less than 360°, thus creating a lengthwise opening to the first lumen.

B. The catheter of A, wherein the catheter material surrounds the second lumen in a cross-sectional dimension.

C. The catheter of A or B, wherein the second lumen has s smaller inner diameter than the first lumen.

D. The catheter of any of A-C, wherein the catheter is configured to be slidably received within a working channel of an endoscope.

E. The catheter of any of A-D, wherein the second lumen is configured to slidably receive a medical device.

F. The catheter of any of A-E, wherein the first lumen is configured to receive an imaging device.

G. The catheter of F, wherein the imaging device comprises a radial ultrasound probe.

H. The catheter of any of A-G, wherein the lengthwise opening of the first lumen is defined by a first flexible edge and a second flexible edge, wherein a first chord measurement between the first and second edges has a first value when the imaging device is not occupying the first lumen, wherein a second chord measurement between the first and second edges has a second value when the imaging device is occupying the first lumen, wherein the first chord measurement is less than the second chord measurement.

I. The catheter of H, wherein the first and second edges exhibit a snap-like action upon receiving the imaging device.

J. A catheter system comprising: a flexible shaft comprising: a first lumen; and a second lumen adjacent to the first lumen; wherein material of the catheter occupies an arc around the first lumen, wherein the arc is greater than 180° and less than 360°, thus creating a lengthwise opening to the first lumen; a cap portion configured to be received at a distal end of the flexible shaft, the cap portion comprising: a first lumen; and a second lumen; and a handle device configured to attach to a proximal end of the flexible shaft, the handle device comprising: a first access port; a second access port; a first lumen in communication with the first access port; and a second lumen in communication with the second access port, wherein the first lumen of the handle device is colinear with the first lumen of the flexible shaft and the second lumen of the handle device is colinear with the second lumen of the flexible shaft.

K. The catheter system of J, wherein the catheter material surrounds the second lumen in a cross-sectional dimension.

L. The catheter system of J or K, wherein the second lumen is smaller than the first lumen.

M. The catheter system of any of J-L, wherein the catheter is configured to be slidably received within a working channel of an endoscope.

N. The catheter system of any of J-M, wherein the second lumen of the flexible shaft and the second access port and the second lumen of the handle device are configured to slidably receive a medical device.

O. The catheter system of any of J-N, wherein the first lumen of the flexible shaft and the first access port and the first lumen of the handle device are configured to receive an imaging device.

P. The catheter system of O, wherein the imaging device comprises a radial ultrasound probe.

Q. The catheter system of any of J-P, wherein the lengthwise opening of the first lumen is defined by a first flexible edge and a second flexible edge, wherein a first chord measurement between the first and second edges has a first value when the imaging device is not occupying the first lumen of the flexible shaft, wherein a second chord measurement between the first and second edges has a second value when the imaging device is occupying the first lumen of the flexible shaft, wherein the first chord measurement is less than the second chord measurement.

R. The catheter system of Q, wherein the first and second edges exhibit a snap-like action upon receiving the imaging device.

The description of the invention is merely exemplary in nature and variations that do not depart from the gist of the invention are intended to be within the scope of the invention. Such variations are not to be regarded as a departure from the spirit and scope of the invention.

What is claimed is:

1. A catheter comprising:
   a first lumen defining a trench, the trench configured to receive an imaging probe collaterally through an opening in the trench; and
   a second lumen adjacent to the first lumen;
   wherein a cross-section of the catheter defines an arc forming the trench of the first lumen, wherein the arc is greater than 180° and less than 360°, thus creating the trench of the first lumen.

2. The catheter of claim 1, wherein material forming the catheter surrounds the second lumen in a cross-sectional dimension.

3. The catheter of claim 1, wherein the second lumen has a smaller inner diameter than the first lumen.

4. The catheter of claim 1, wherein the catheter is configured to be slidably received within a working channel of an endoscope.

5. The catheter of claim 4, wherein the second lumen is configured to slidably receive a medical device.

6. The catheter of claim 4, wherein the first lumen is configured to receive an imaging device.

7. The catheter of claim 6, wherein the imaging device comprises probe.

8. The catheter of claim 7, wherein the probe comprises a radial ultrasound probe.

9. The catheter of claim 6, wherein the trench of the first lumen is defined by a first flexible edge and a second flexible edge,
   wherein a first chord measurement between the first and second edges has a first value when the imaging device is not occupying the first lumen,
   wherein a second chord measurement between the first and second edges has a second value when the imaging device is occupying the first lumen,
   wherein the first chord measurement is less than the second chord measurement.

10. The catheter of claim 9, wherein the first and second edges exhibit a snap-like action upon receiving the imaging device.

11. A catheter system comprising:
    a flexible shaft comprising:
       a first lumen defining a trench, the trench configured to receive an imaging probe collaterally through an opening in the trench; and
       a second lumen adjacent to the first lumen;
       wherein material of the catheter occupies an arc around the first lumen, wherein the arc is greater than 180° and less than 360°, thus creating the trench of the first lumen;
    a cap portion configured to be received at a distal end of the flexible shaft, the cap portion comprising:
       a probe lumen; and
    a handle device configured to attach to a proximal end of the flexible shaft, the handle device comprising:
       a first access port;
       a second access port;
       a first handle lumen in communication with the first access port; and
       a second handle lumen in communication with the second access port,
    wherein the first handle lumen is colinear with the first lumen of the flexible shaft and the second handle lumen colinear with the second lumen of the flexible shaft.

12. The catheter system of claim 11, wherein material forming the catheter surrounds the second lumen in a cross-sectional dimension.

13. The catheter system of claim 11, wherein the second lumen is smaller than the first lumen.

14. The catheter system of claim 11, wherein the catheter is configured to be slidably received within a working channel of an endoscope.

15. The catheter system of claim 14, wherein the second lumen of the flexible shaft and the second access port and the second lumen of the handle device are configured to slidably receive a medical device.

16. The catheter system of claim 14, wherein the first lumen of the flexible shaft and the first access port and the first handle lumen are configured to receive an imaging device.

17. The catheter system of claim 16, wherein the imaging device comprises a probe.

18. The catheter system of claim 17, wherein the probe comprises a radial ultrasound probe.

19. The catheter system of claim 16, wherein the trench of the first lumen is defined by a first flexible edge and a second flexible edge,
    wherein a first chord measurement between the first and second edges has a first value when the imaging device is not occupying the first lumen of the flexible shaft,
    wherein a second chord measurement between the first and second edges has a second value when the imaging device is occupying the first lumen of the flexible shaft,
    wherein the first chord measurement is less than the second chord measurement.

20. The catheter system of claim 19, wherein the first and second edges exhibit a snap-like action upon receiving the imaging device.

* * * * *